United States Patent [19]

Carlson et al.

[11] 4,441,361

[45] Apr. 10, 1984

[54] METHOD AND APPARATUS FOR MEASUREMENT OF FLUID DENSITY AND FLOW RATES IN MULTI-PHASE FLOW REGIMES

[75] Inventors: Norman R. Carlson; Raymond E. Roesner, both of Houston; Edward W. Lanuke, Spring, all of Tex.

[73] Assignee: Dresser Industries, Inc., Dallas, Tex.

[21] Appl. No.: 307,714

[22] Filed: Oct. 2, 1981

[51] Int. Cl.³ .................. E21B 47/00; G01F 13/00
[52] U.S. Cl. ............................ 73/155; 73/861.04
[58] Field of Search ............ 73/32 R, 61.1 R, 861.04, 73/155

[56] References Cited

U.S. PATENT DOCUMENTS

| | | | |
|---|---|---|---|
| 2,649,711 | 8/1953 | Dale | 73/155 |
| 3,113,455 | 12/1963 | Sloan et al. | 73/155 |
| 3,162,042 | 12/1964 | Hart | 73/155 |
| 3,176,511 | 4/1965 | Widmyer | 73/155 |
| 3,246,145 | 4/1966 | Higgins | 73/61.1 R |
| 3,258,963 | 7/1966 | Bryant et al. | 73/861.04 X |
| 3,371,527 | 3/1968 | Moulin | 73/155 |
| 3,721,121 | 3/1973 | Fierfort | 73/155 |
| 3,905,226 | 9/1975 | Nicolas | 73/155 |
| 3,942,374 | 3/1976 | Glenn, Jr. | 73/155 |
| 3,982,433 | 9/1976 | Stout | 73/155 |

OTHER PUBLICATIONS

Advertising Brochure, Resource Systems Company, Jul. 1981, p. 4.

*Primary Examiner*—Charles A. Ruehl
*Attorney, Agent, or Firm*—Richard M. Byron; Patrick H. McCollum

[57] ABSTRACT

In a well containing a multi-phase fluid flow regime is disposed an elongated body member with a funnel configuration attached thereto for the purpose of collecting and mixing the multiple fluid phases. An aperture is provided in the body member, proximate to the apex of the funnel configuration, to allow discharge of the substantially homogeneous mixture of the fluid phases from the funnel through a passage in the body member. A rotor is acted upon by the flow of this mixture and generates a signal representative of the mixture flow rate. A portion of the mixture then enters a chamber in the elongated body member wherein a measurement is made of the degree of penetration of the mixture achieved by gamma radiation, thereby yielding a measurement representative of the density of the mixture. The flow rates and volumetric fractions of each of the individual phases may then be determined in accordance with the mixture density and total flow rate.

16 Claims, 7 Drawing Figures

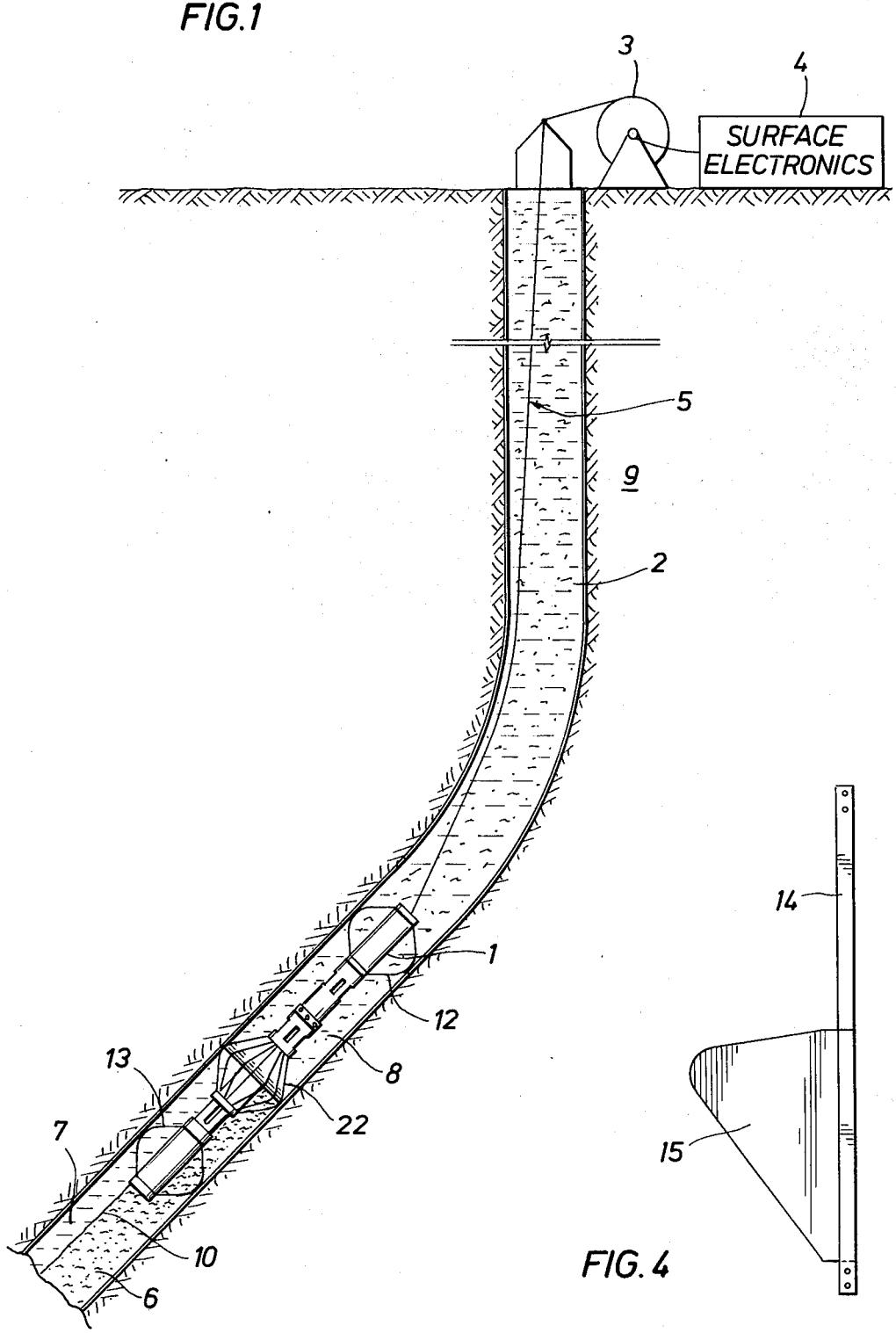

FIG.2A
FIG.2B
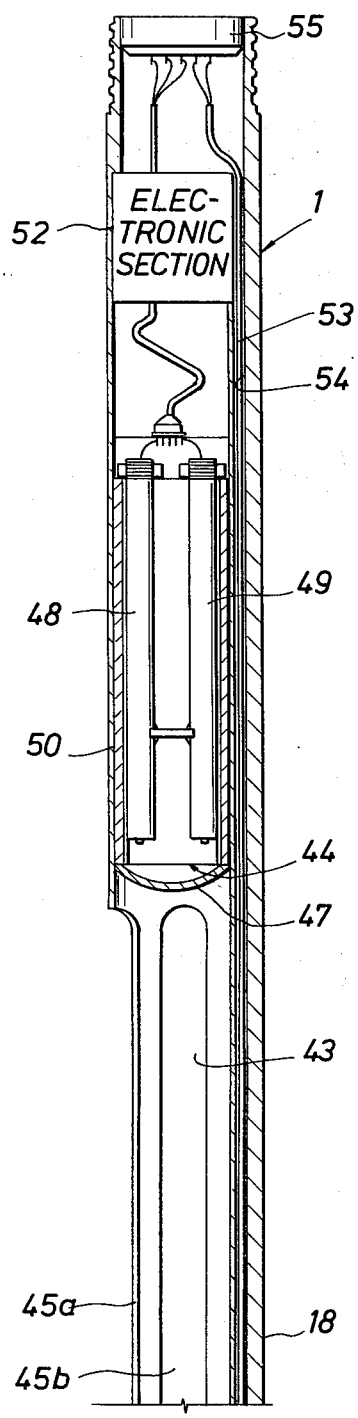
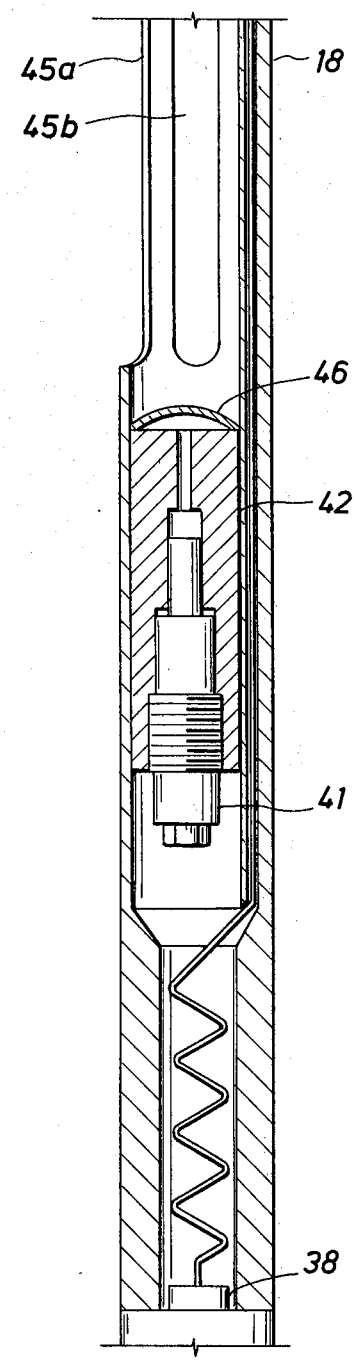

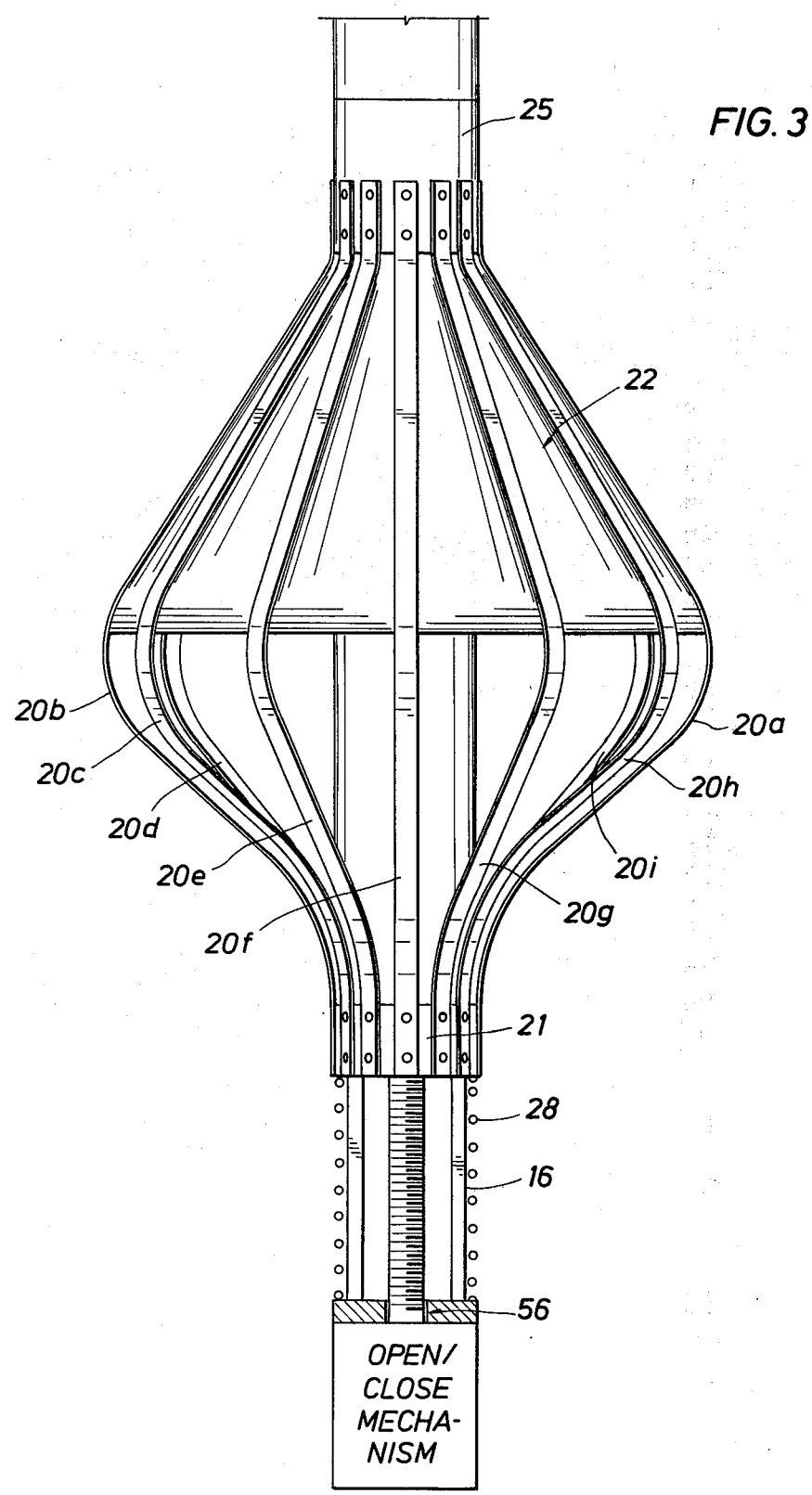

METHOD AND APPARATUS FOR MEASUREMENT OF FLUID DENSITY AND FLOW RATES IN MULTI-PHASE FLOW REGIMES

BACKGROUND OF THE INVENTION

This invention relates generally to methods and apparatus for determining the density and flow rates of fluid in a well or pipe and, more specifically, to methods and apparatus for determining the average density and individual flow rates of the different components of a fluid flow regime consisting of more than one fluid phase.

In producing wells it is common to find the well fluid consisting of multiple phases, such as oil and water, oil and gas, or oil, water, and gas. Often, one or more of these phases is an undesirable segment of the well production. For example, in the case of a flow regime consisting of oil and water, as is common in such producing wells, the oil is the fluid phase desired to be produced while the water phase is typically an undesired element in the production flow. When the degree of water present in the production flow becomes excessive, logging surveys are run to determine the locations and rates of the water entry into the flow regime. These surveys include measurements of the flow rate and attempts at determining the average density of the well fluid at a survey depth. Using these measurements and data derived at the earth's surface of the densities of the individual phases, determinations are made of the volumetric fractions of water and oil in the flow, such fractions aiding the determination of the locations and rates of water entry. From these determinations remedial actions to control the water entry may be chosen.

Measurement of the flow rate and density of the well fluid is complicated by the fact that not only do the individual phases of the flow regime flow at different velocities, referred to as phase slippage, but also the nature of the flow pattern is not uniform throughout cross-sections of the pipe. This non-uniformity of the flow pattern is caused by one or more of a multiplicity of phenomena which are known in the art, such as, for example, stagnation, heavy-phase fall-back, and circulation, and is accentuated by such factors as large pipe, low flow rates, and/or deviated boreholes.

One means known to the oil and gas industry to measure the flow rate in a producing well is to use a packer-type flowmeter. These flowmeters consist of a packer mechanism which is lowered in the borehole to the desired survey depth and locked into position, blocking the fluid flow around the device and causing the fluid to flow through an aperture in the packer which contains, or is coupled to, a means for measuring the rate of the fluid flow. These packer-type flowmeters are often difficult to properly secure in position and to remove after the measurement has been taken and typically may not be used in wells having relatively high flow rates because the pressure of the fluid flow will cause the packer to unseat from its established position. Further, where the fluid flow regime consists of two or more phases traveling at different velocities, it is believed that the relative composition of the fluid flow regime, and therefore the overall measured flow rate, is altered by the abrupt blockage of the fluid flow path by the packer.

Another means by which the oil and gas industry has attempted to determine both flow rates and densities has been to intersect the fluid flow regime with the appropriate logging instrument while allowing the fluid flow to continue around the instrument. This type of measurement has been taken with the logging instrument either centralized within the borehole or allowed to decentralize and rest along the lower side of the borehole. It can be appreciated that this type of measuring only determines the flow rate or density of such portion of the fluid flow regime as actually engages the measuring system of the logging instrument. Therefore, fluid phases which do not intersect the instrument or non-uniformities in the flow pattern, caused by effects such as those described above, which occur in the flow regime may cause the readings from the logging instrument to yield less than optimal data as to the nature of the fluid flow regime. Additionally, the accuracy of this type of surveying may be further complicated by the unknown effects upon the multi-phase flow regime when a logging tool is introduced into the producing well.

Accordingly, the present invention overcomes the deficiencies of the prior art by providing an apparatus and method whereby the average density of a multi-phase flow regime may be determined from a single measurement while minimizing phenomena which would disturb the accuracy of the measurement, and, whereby the volumetric fractions and the flow rates of the individual phases of the flow regime may be more accurately determined in accordance with the density measurement thus obtained.

SUMMARY OF THE INVENTION

The present invention provides a method and an apparatus for use in connection with a well or pipe containing a multi-phase fluid flow regime, such apparatus being constructed upon an elongated member extending from the elongated member is a funnel configuration which collects and accelerates the multi-phase fluid flow and causes it to blend into one substantially uniform mixture. The mixture is discharged from the funnel past a rotor assembly which generates a signal indicative of the flow rate of the mixture. The mixture is then expelled back into the well. Apertures in the instrument provide fluid communication between a chamber within the instrument and the well, allowing the mixture enter to the chamber. A gamma ray source and detector are located at opposite ends of the chamber. The detector generates a signal representative of the penetration of the gamma rays from the source through the mixture sample in the chamber. This measurement is correlated to measurements of gamma ray penetration taken by that source and detector through substances of known density, such correlation allowing the determination of the actual density of the surveyed sample.

Using the data thus obtained, plus derived data of the densities of the individual phases, the volumetric fractions of the fluid phases as related to the total flow regime may be determined. Similarly, the flow rates of each of the phases may be derived as a function of the relative volumetric fractions of each phase and of the total flow rate.

Accordingly, it is a feature of the present invention to provide a new and improved method and apparatus for determining the average density of a multi-phase flow regime.

It is still another feature of the present invention to provide a new and improved method and apparatus for determining the volumetric fractions of the components present in a multi-phase flow regime.

It is still another feature of the present invention to provide a new and improved method and apparatus for determining the flow rates of the components present in a multi-phase flow regime.

BRIEF DESCRIPTION OF THE DRAWINGS

FIG. 1 is a side elevational view, partly in cross-section, of an apparatus for detecting densities and flow rates in accordance with this invention, disposed within a producing well.

FIGS. 2A-D are a schematic view, partly in cross-section, of the apparatus of FIG. 1.

FIG. 3 is a side view of the portion of the apparatus shown in FIG. 2D, shown partially in cross-section and illustrated in operating configuration.

FIG. 4 is a pictorial representation of a deflector spring of the detecting apparatus of the present invention.

DETAILED DESCRIPTION OF THE PREFERRED EMBODIMENT

Figure 2C:
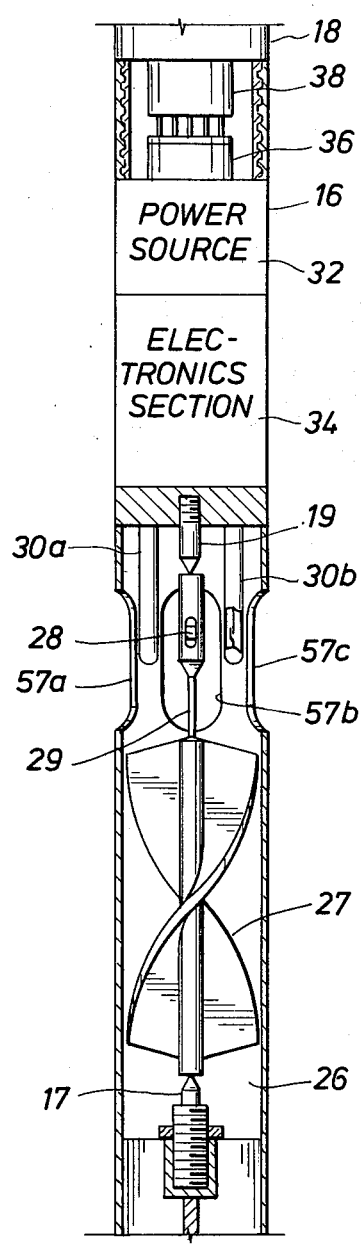

Referring now to the drawings in more detail, especially to FIG. 1, there is illustrated a deviated cased borehole 2, penetrating an earth formation 9, shown in cross-section, It is to be understood that although the illustration shows a borehole in which casing has been set, the present invention may also be employed in an uncased borehole. Disposed within the borehole 2, and suspended from cable 5, is an apparatus for measurement of fluid density and flow rates in multi-phase flow regimes in accordance with the present invention. The apparatus is positioned in the center of the borehole by centralizers 12 and 13. At the earth's surface there is illustrated a hoist 3 and surface electronics 4 in a configuration well known in the well logging art. Shown in the borehole 2, below the density-flowmeter instrument 1, is a two-phase fluid flow, illustrated generally at 10, such flow is common in producing wells. Where the two-phase fluid flow 10 consists of water and oil, as is also common in such producing wells, the water 6 will flow toward the lower side of the well bore while the oil 7 flows above due to its lesser density. Above the density-flowmeter instrument 1 in the well 2, this previously two-phase fluid flow is shown as an essentially uniform mixture 8 due to the operation of the instrument 1 as will be described later herein.

Referring now to FIGS. 2A-D of the drawings, there is shown the density-flowmeter instrument 1 in greater detail and in cross section. The instrument 1 is constructed upon two elongated body members 16 and 18 joined together, threadably or by other suitable means, and adapted to traverse an earth borehole.

Figure 2D:
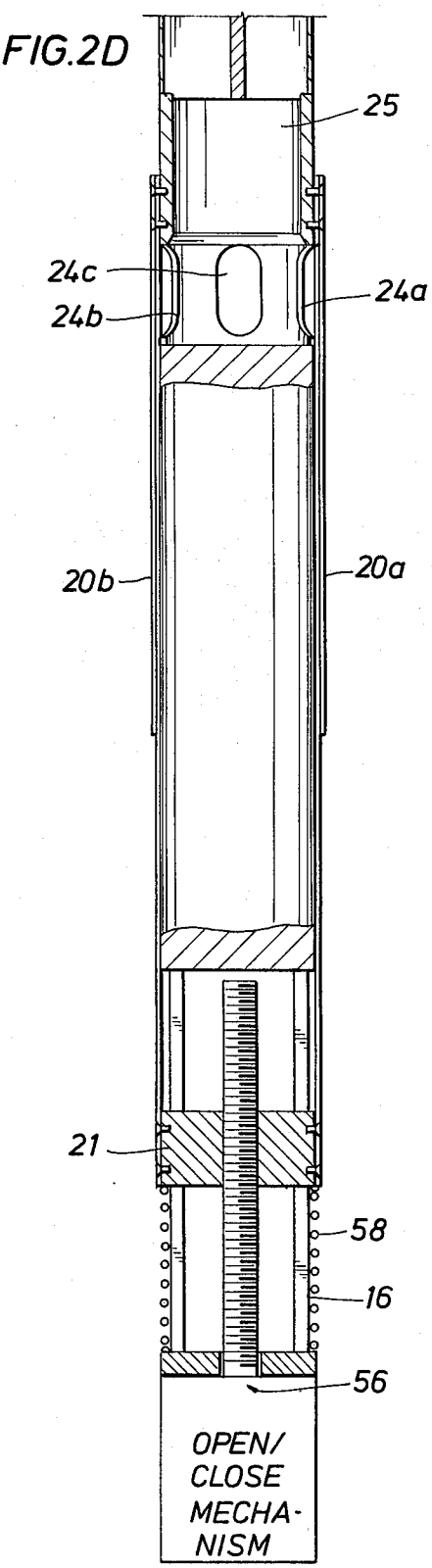

Referring now to FIG. 3, there is illustrated the portion of the density flowmeter instrument of FIG. 2D, shown in operating configuration and partly in cross-section. In the preferred embodiment, a plurality of deflector springs 20a, 20b, 20c, 20d, 20e, 20f, 20g, 20h and 20i are disposed essentially equidistantly around the periphery of lower body member 16. Each deflector spring 20a, 20b, 20c, 20d, 20e, 20f, 20g, 20h or 20i is comprised of an elongated bow spring, 14 in FIG. 4, with a deflector fin, 15 in FIG. 4, firmly affixed thereto by spot welding or other suitable means. These deflector springs 20a, 20b, 20c, 20d, 20e, 20f, 20g, 20h and 20i are interlayed with one another, the laterally extending portion of the spring fitting below or closer to the body member 16 than the spring immediately to its side. The preferred embodiment would have approximately 10-14 of these deflector springs, and most preferably would have 12 deflector springs. Each of these springs 20a, 20b, 20c, 20d, 20e, 20f, 20g, 20h, 20i has a first end fixedly mounted toward the proximal end of lower body member 16 and a second end mounted to collar 21 which is slidably mounted on lower body member 16. Attached to collar 21 is a motor-driven, screw-type, open/close mechanism of a type known in the art, indicated generally at 56. This open/close mechanism 56 is actuated by means of a control signal from the surface electronics 4, and is designed to move collar 21 toward the proximal end of the instrument 1, as illustrated in FIG. 3, and, upon command from the surface electronics 4, to withdraw collar 21 back toward the distal end of the instrument, as shown in FIG. 2D.

Referring again to FIG. 3, when collar 21 is located toward the proximal end of the instrument 1, deflector springs 20a, 20b, 20c, 20d, 20e, 20f, 20g, 20h, 20i are forced out and away from lower body member 16. This causes the deflector springs 20a, 20b, 20c, 20d, 20e, 20f, 20g, 20h, 20i acting together, to form a generally tapered collector 22, most preferably a funnel configuration, virtually blocking the passage of fluid around the instrument 1 in the well 2 (shown in FIG. 1). The function of this tapered collector 22 will be described herein more fully in the discussion of the operation of the instrument.

Referring again to FIG. 2, particularly to FIGS. 2C-D, inside the bore and proximate the apex of the aforementioned tapered collector (illustrated at 22 in FIG. 3), are located a plurality of entrance apertures 24a, 24b, 24c preferably spaced essentially equidistantly around the periphery of lower body member 16. These entrance apertures 24a, 24b, 24c connect with passage 25, further connecting to rotor chamber 26 in lower body member 16 to provide fluid communication between the collector 22 and rotor chamber 26. Referring now particularly to FIG. 2C, rotor chamber 26 contains a rotor 27 freely rotatably mounted on a longitudinal axis between two opposing pivots 17 and 19. Associated with rotor 27 is a measuring device for detecting the rotational speed of the rotor 27. In the preferred embodiment this measuring device is a combination of a magnet 28 mounted on the rotor trunnion 29 and a plurality of magnetic reed switches 30a, 30b disposed in proximity to and around the trunnion 29. These reed switches 30a, 30b are connected to a suitable power source 32, preferably a 25 volt d.c. power source, so that as the magnet 28 passes each switch 30a, 30b, the switch alternately opens and closes, thereby generating an electrical pulse representative of one rotation of the trunnion 29 past that individual switch 30a or 30b. The pulses from the switches 30a and 30b are then coupled to electronics section 34 to generate a first electrical signal representative of the rotational speed of the rotor 27. The electronics section 34 then amplifies this signal by means of a conventional line driver circuit to prepare the signal for transmission to the surface electronics 4. This first electrical signal is coupled to an electrical connector 36 matable with a complimentary connector 38 in upper body member 18. These connectors 36 and 38 facilitate disassembly of the instrument by allowing the uncoupling of upper body member 18 from lower body member 16 while providing electrical coupling therebetween. This disassembly is designed to ease in transportation of the instrument and facilitates the removal and installation of nuclear source 41 within upper body member 18 (illustrated in FIG. 2B).

Referring now to FIGS. 2A–B, nuclear source 41 is preferably a chemical gamma ray source, most preferably a Cesium-137 source emitting gamma rays with an energy of approximately 0.661 Mev. Source 41 is mounted in a block 42 within upper body member 18. This block 42 is constructed of a suitably dense material, preferably tungsten, to collimate the gamma radiation emitted by source 41 into a beam which longitudinally traverses upper body member 18 to impinge detector 44. Located in upper body member 18 between source 41 and detector 44, is a chamber 43, with a plurality of apertures 45a, 45b formed in upper body member 18 to allow free-flowing fluid communication between chamber 43 and the well. Both source 41 and detector 44 are isolated from the chamber 43 by pressure domes 46 and 47. These domes 46, 47 are constructed of a suitable material, preferably steel, and of such thickness so as to withstand the pressure in the well and protect source 41 and detector 44 from the well environment while still allowing penetration of the gamma radiation. Detector 44 consists of a means for detecting the radiation emitted by source 41, preferably one or more Geiger tubes or, alternatively, a scintillation crystal and photomultiplier tube, most preferably consisting of a plurality of Geiger tubes 48, 49 which emit electrical impulses when impinged by gamma rays from source 41. Detector 44 is surrounded on the sides by suitable shielding 50, preferably tungsten shielding, to minimize the impinging of detector 44 by radiation other than that emitted by source 41, such as radiation occurring naturally in the earth formation surrounding the borehole. These Geiger tubes 48, 49 are connected in parallel to sum their outputs. The summed output of the Geiger tubes; ie, the detector output, is coupled to an electronics section 52 which amplifies this signal by means of a conventional line driver circuit to prepare this second electrical signal for transmission up cable 5 to the surface electronics 4. Also contained in upper body member 18 is a longitudinal passage 54 containing one or more electrical conductors 53 suitable for carrying electrical signals from lower end electrical connector 38 to the cablehead connector 55 at the proximal end of upper body member 18.

It is known in the art of well logging to determine the density of a substance through the use of gamma radiation. Gamma rays are electromagnetic radiations which have the capability of penetration through matter. As gamma radiation passes through a sample of matter, some of the radiation will fail to fully penetrate the sample. Decreases in this penetration occur predominately due to the effects of three interactions; photoelectric absorbtion, compton scattering, and pair production, all of which occur in degrees relative to the density of the irradiated matter. Therefore, penetration bears an inverse relationship to the density of the matter, such that the greater the density of the substance, the smaller the penetration.

It is possible to measure this decrease in penetration and therefore the density of a sample of matter by causing a beam of gamma rays from a radiation source to pass through the sample and strike a detector. Due to the effects described above, not all of the emitted gamma rays will reach the detector. By correlating the measured gamma ray penetration through that matter with calibration measurements of gamma ray penetration for the source and detector through substances of known densities the density of the sample may be determined.

It can be readily appreciated that such a density measurement only measures the gamma ray penetration through matter which actually intersects the beam of radiation. Therefore, it can also be readily appreciated that when attempting to measure the average density of fluid in a well when such fluid consists of two or more phases, the source and detector must encounter the various phases in a manner indicative of the relative percentage which each phase represents of the total well fluid flow. The present invention accomplishes this requisite by uniformly mixing the fluid phases, thereby providing a substantially homogeneous sample through which the gamma ray penetration may be measured.

Referring now to the Figures generally, in the normal operation of the density-flowmeter apparatus, the instrument 1 is lowered in the well 2 to the depth at which a measurement is desired. The surface electronics 4 are utilized to actuate the open/close mechanism 56 in the instrument, pushing collar 21 toward the proximal or uphole end of lower body member 16 and causing deflector springs 20a, 20b, 20c, 20d, 20e, 20f, 20g and 20h to form a funnel configuration 22 as described above. This funnel 22 virtually blocks the flow of fluid around the instrument 1 channeling the fluid toward the apertures 24a, 24b 24c and passage 25 in lower body member 16 which form the throat of the funnel 22. It is to be appreciated that as the funnel 22 narrows, due to the constant flow rate of the fluid, the linear speed of the fluid increases. As the accelerating fluid phases converge toward the throat of the funnel 22, a turbulence is created causing the individual phases to blend together into a single mixture of at least substantially uniform composition. Additionally, the gradual channeling accelerates the fluid flow without disturbing the relative flows of the fluid phases as they exist below the instrument 1. This non-disturbance allows the creation of a substantially homogeneous mixture of the phases without significantly disturbing the relative composition of the mixture as compared with the relative composition of the flow regime below the instrument 1.

This mixture then travels through passage 25 to rotor chamber 26. The mixture passes and contacts rotor 27 causing it to rotate, the exact rotational speed being dependent upon and indicative of the total flow rate of the fluid in the well. The rotational speed of the rotor 27 is detected and converted into a plurality of pulsed electrical signals which are then summed and amplified by the electronics section 34 into a first electrical signal as described above. This signal is then transmitted over cable 5 to the surface electronics 4. Simultaneously with providing an indication of the fluid flow rate, the rapid rotation of rotor 27 serves to further enhance the blending of the multiple phases of fluid into one substantially uniform mixture. This mixture 8 then passes through exit apertures 57a, 57b, 57c and returns to the well bore 2.

A portion of the mixture then passes through apertures 45a and 45b and enters density measuring chamber 43 where the mixture is traversed by a beam of gamma radiation. That radiation which traverses the chamber and the mixture therein impinges detector 44 yielding a second electrical signal representative of the relative density of the mixture as previously described. This second signal is then transmitted over cable 5 to the surface electronics 4.

At the surface this second signal representing the relative density of the substantially homogeneous mixture may be compared to a scale established with calibration measurements taken before the instrument was lowered into the borehole. These calibration measurements of gamma ray penetration are taken through substances of known density such as water and air. By correlating the measurements represented by the second signal to the scale established by these calibration measurements, a determination may be made of the actual density of the surveyed fluid.

The data thus obtained from the two signals allows a functional determination to be made of the volumetric fraction of each of the phases present in the well fluid, particularly when the well fluid consists of two phases, as is illustrated herein. The volumetric fraction of the heavy phase, ($Y_H$) may be determined by the relation set forth by the equation:

$$Y_H = a \cdot \rho_M + b \tag{1}$$

where $\rho_m$ represents the density of the uniform mixture as determined from the second signal, that signal generated by detector 44, and a and b are parameters determined from the densities of the individual phases. Parameter a is represented by:

$$a = \frac{1}{\rho_H - \rho_L} \tag{2a}$$

while parameter b is represented by $$b = \frac{-\rho_L}{\rho_H - \rho_L} \tag{2b}$$

where $\rho_H$ represents the density of the heavy phase and $\rho_L$ represents the density of the light phase of the well fluid. These terms, $\rho_H$ and $\rho_L$, may be determined by fluid samples taken at the surface of the well. However, in equation 1 all densities must be at equivalent conditions of temperature and pressure, therefore, either $\rho_H$ and $\rho_L$ must be correlated to downhole survey conditions or $\rho_M$ must be converted to an equivalent value under surface conditions, either adjustment being accomplished using correlations familar to the well logging art.

The solution of equation 1 yields the volumetric percentage of the heavy phase represented in the well fluid at the depth of the density measuring chamber. The volumetric fraction of the light phase ($Y_L$) expressed as a function of the heavy phase, is determined by:

$$Y_L = 1 - Y_H \tag{3}$$

The flow rates of the individual phases may be determined in accordance with the volumetric fractions determined by the relationships expressed in equations 1 and 3. In wells having either a small diameter or a high flow rate the percentage of the total flow rate represented by the individual phases will essentially correlate to the volumetric fractions and therefore may be determined in accordance with relationships similar to those expressed in equations 1 and 3. Therefore, the percentages of the heavy phase and the light phase present in the total flow rate (represented as %H and %L, respectively) may be expressed as the relations $$\%H = 100 (a\rho_M + b) \tag{4}$$

and $$\%L = 100 - \%H \tag{5}$$

However, in wells having lower flow rates or larger diameters the correlation between the percentage of the total flow rate represented by each of the phases and the density of the uniform mixture $\Sigma_M$ tends to depart from the linear relationships represented in equations 4 and 5. Additionally, the degree of this departure is highly influenced by any incline or deviation from vertical of the borehole, this departure being a tendency for the linear relationship expressed in equation 4 to indicate the presence of a greater percentage of the heavy phase than actually exists. Therefore, to correct for this departure a correction term is subtracted from equation 4, yielding the equation:

$$\%H = 100 (a \rho_M + b) - \frac{25620 A}{BPD_T} \cdot F(\rho_M) \tag{6}$$

where A is the area of the annulus open to fluid flow between the instrument and the borehole, $BPD_T$ represents the total barrels per day flow which is represented by the first signal generated by the measurement of the rotation of rotor 27, and 25620 is a conversion factor to convert cubic feet per minute into barrels per day multiplied by 100 for percentage calculation. Term $F(\rho_M)$ is a function of the density of the heavy phase ($\rho_H$), the density of the light phase ($\rho_L$), and the slip velocity between the two phases.

The barrels per day flow rates of the light and heavy phases in the flow regime may then be computed by solving, respectively:

$$BPD_L = \frac{\%L \cdot BPD_T}{100} \tag{7a}$$

and $$BPD_H = \frac{\%H \cdot BPD_T}{100} \tag{7b}$$

While the above has shown and described the preferred embodiments of this invention, it will be apparent to those skilled in the art that many changes and modifications may be made without departing from the invention in its broader aspects. Accordingly, it should be clearly understood that the forms of the invention described and illustrated are exemplary only and are not intended as limitations on the scope of the present invention and that the claims are intended to cover any and all changes and modifications as may be made within the true spirit and scope of this invention.

The embodiments of the invention in which an exclusive property or privilege is claimed are defined as follows:

1. An apparatus for detecting the mixture density of a fluid flow regime having at least two phases, said flow regime moving through a borehole, comprising:
   an elongated tubular housing adapted to traverse said borehole;
   a tapered collector affixed to said housing for intersecting at least a portion of said flow regime for causing said flow regime to accelerate and produce a substantially uniform mixture of said flow regime;
   said collector formed by a plurality of deflector members disposed essentially equidistantly around said housing in interlayered fashion, each deflector member including an elongated bow spring and a fin portion extending therefrom;

said collector having at least one aperture proximate the apex of said collector for discharging said accelerated and substantially uniform mixture from said collector;

a nuclear source for emitting gamma radiation;

a mounting block constructed of relatively dense material for mounting said source within said housing;

a chamber traversed by said gamma radiation within said housing, said chamber having at least one aperture for fluidly communicating with said borehole and for containing a sample of said substantially uniform mixture;

at least one radiation detector for emitting a signal when impinged by gamma radiation, said detector positioned within said housing to detect gamma radiation traversing said chamber;

a tungsten shield surrounding said radiation detector; and a pair of generally dome-shaped members covering said source and said detector respectively for fluidly isolating said source and said detector from said chamber.

2. The apparatus of claim 1, further comprising:

a rotor mounted within said housing for rotation in functional relation to the flow of said mixture from said tapered collector;

at least one magnet mounted on said rotor; and at least one electrical switch responsive to said magnet for generating an electrical signal functionally related to the rotational speed of said rotor.

3. A method of measuring the volumetric fractions of the individual phases of a fluid flow regime having at least two phases, comprising the steps of:

mixing at least a portion of the flow to produce a mixture of substantially uniform composition;

measuring the density of said mixture of substantially uniform composition;

determining the density of the individual phases of the flow regime; and determining the volumetric fraction of each individual phase of said mixture, in accordance with the measured mixture density and the density of the individual phases of the flow regime.

4. The method of measuring the volumetric fractions of the individual phases of a fluid flow regime having at least two phases of claim 3, wherein said volumetric fraction for one phase is determined in accordance with the relationship:

$$Y = a \cdot \rho_M + b$$

where $\rho_M$ represents the density of said mixture and a and b are determined from the densities of said individual phases.

5. The method of measuring the volumetric fractions of the individual phases of a fluid flow regime having at least two phases of claim 4, wherein a is determined in accordance with the relationship:

$$a = \frac{1}{\rho_H - \rho_L}$$

and b is determined in accordance with the relationship:

$$b = \frac{-\rho_L}{\rho_H - \rho_L}$$

where $\rho_H$ and $\rho_L$ represent the density of the heavy and light phases.

6. A method of measuring the flow rates of the individual phases of a fluid flow regime having at least two phases, comprising the steps of:

mixing at least a portion of the flow to produce a mixture of substantially uniform composition;

measuring the density of said mixture of substantially uniform composition;

measuring the density of each phase of the fluid flow regime;

determining the volumetric fraction of each phase of said mixture of substantially uniform composition, in accordance with the measured mixture density and the density of each phase;

measuring the flow rate of said mixture of substantially uniform composition; and determining the flow rate of each phase of the flow regime, at least in accordance with the measured flow rate of said mixture and said phase's volumetric fraction of said mixture.

7. The method of measuring the flow rates of the individual phases of a fluid flow regime of claim 6, wherein the step of determining the volumetric fraction of each phase of the flow regime further comprises;

measuring the densities of the individual phases of said flow regime; and determining the volumetric fraction of each phase of the flow regime at least in accordance with the measured density of said mixture of substantially uniform composition and the measured densities of the individual phases of said flow regime.

8. The method of measuring the flow rates of the individual phases of a fluid flow regime of claim 7 wherein the step of determining the flow rate of each phase further comprises correcting said flow rate of each phase of said flow regime to account for at least the effect of slippage between the phases.

9. A method for determining characteristics of a fluid flow regime having at least two phases, said flow regime moving through a pipe, comprising the steps of:

accelerating the fluid flow regime through a generally tapered collector to blend said flow regime into a substantially homogeneous mixture;

determining the density of said substantially homogeneous mixture;

measuring the density of each phase of said fluid flow regime; and determining the volumetric fractions of each phase of said fluid flow regime in accordance with a linear relation between the measured densities of each phase of said fluid flow regime and said density of said substantially homogeneous mixture of said flow regime.

10. The method for determining characteristics of a fluid flow regime having at least two phases of claim 9, wherein the method further comprises:

measuring the flow rate of said substantially homogeneous mixture; and determining the flow rate of each phase of said fluid flow regime in accordance with said measured flow rate of said substantially homogeneous mixture and said volumetric fractions of each phase in said mixture.

11. The method for determining characteristics of a fluid flow regime having at least two phases of claim 10, wherein the method further comprises:
determining a correction term to account at least for the effect of slippage between the phases of said flow regime in accordance with the measured densities of the individual phases of said flow regime; and
determining the flow rates of the phases of said flow regime at least in accordance with the measured flow rate of said mixture, said volumetric fractions of each phase in said mixture and said correction term.

12. The method for determining characteristics of a fluid flow regime having at least two phases of claim 9, wherein the method further comprises:
measuring the flow rate of said substantially homogeneous mixture; and
determining the flow rate of each phase of said fluid flow regime in accordance with the measured flow rate of said substantially homogeneous mixture, the density of said substantially homogeneous mixture, said volumetric fractions of each phase in said mixture and said densities of each phase of said flow regime.

13. The method for determining characteristics of a fluid flow regime having at least two phases of claim 12, wherein the method further comprises:
determining a correction term to account at least for the effect of slippage between the phases of said flow regime in accordance with the measured densities of the individual phases of said flow regime; and
determining the flow rates of the components of said flow regime at least in accordance with the measured flow rate of said substantially homogeneous mixture, the density of substantially homogeneous mixture, said volumetric fractions of each phase in said mixture, said densities of each phase of said flow regime and said correction term.

14. The method for determining characteristics of a fluid flow regime having at least two phases of claim 9, wherein said volumetric fraction for one phase is determined in accordance with the relationship:

$$Y = a \cdot \rho_M + b$$

where $\rho_M$ represents the density of said mixture and a and b are determined from the densities of said individual phases.

15. The method for determining characteristics of a fluid flow regime having at least two phases of claim 14, wherein a is determined in accordance with the relationship:

$$a = \frac{1}{\rho_H - \rho_L}$$

and b is determined in accordance with the relationship:

$$b = \frac{-\rho_L}{\rho_H - \rho_L}$$

where $\rho_H$ and $\rho_L$ represent the density of the heavy and light phases.

16. A method of measuring the flow rates of the individual phases of a fluid flow regime having at least two phases, comprising the steps of:
mixing at least a portion of the flow to produce a mixture of substantially uniform composition;
measuring the density of said mixture of substantially uniform composition;
determining the volumetric fraction of each phase of said mixture of substantially uniform composition at least in accordance with the measured mixture density;
measuring the flow rate of said mixture of substantially uniform composition; and
determining the flow rate of each phase of the flow regime, said flow rate of each phase determined by;
determining a correction term to account at least for the effect of slippage between the phases of said fluid flow regime in accordance with the measured density of the individual phases of said flow regime; and
measuring the flow rates of the phases of said flow regime at least in accordance with the measured flow rate of said mixture, each phase's volumetric fraction of said mixture and the correction term accounting for at least the effect of slippage between the phases.

* * * * *